US007214375B1

(12) United States Patent
Border et al.

(10) Patent No.: US 7,214,375 B1
(45) Date of Patent: May 8, 2007

(54) METHODS OF DECREASING THE ACCUMULATION OF EXTRACELLULAR MATRIX ASSOCIATED WITH GLOMERULONEPHRITIS WITH ANTI-TGF-β-SPECIFIC ANTIBODIES (75) Inventors: Wayne A. Border, Salt Lake City, UT (US); Erkki I. Ruoslahti, Ranco Santa Fe, CA (US)

(73) Assignee: La Jolla Cancer Research Foundation, La Jolla, CA (US)

( * ) Notice: Subject to any disclaimer, the term of this patent is extended or adjusted under 35 U.S.C. 154(b) by 0 days.

(21) Appl. No.: 08/349,479

(22) Filed: Dec. 2, 1994

Related U.S. Application Data (63) Continuation of application No. 08/196,892, filed on Feb. 14, 1994, now abandoned, which is a continuation of application No. 07/416,656, filed on Oct. 3, 1989, now abandoned, which is a continuation-in-part of application No. 07/415,081, filed on Sep. 29, 1989, now abandoned.

(51) Int. Cl.
A61K 39/395 (2006.01)
C07K 16/24 (2006.01)

(52) U.S. Cl. .............. 424/145.1; 424/130.1; 424/141.1; 424/158.1; 530/387.1; 530/388.1; 530/388.2; 530/388.23

(58) Field of Classification Search .............. 435/7; 424/85.8, 130.1, 141.1, 158.1; 530/382.1, 530/388.23
See application file for complete search history.

(56) References Cited

U.S. PATENT DOCUMENTS

| 5,571,714 A | 11/1996 | Dasch et al. ........... 435/240.27 |
| 5,583,103 A * | 12/1996 | Ruoslahti et al. |
| 5,772,998 A | 6/1998 | Dasch et al. ............. 424/133.1 |
| 5,783,185 A | 7/1998 | Dasch et al. ............. 424/133.1 |
| 5,824,655 A * | 10/1998 | Border ........................ 514/44 |

FOREIGN PATENT DOCUMENTS

| EP | 282317 A2 | 9/1988 |
| WO | WO88/03151 | 5/1988 |

OTHER PUBLICATIONS

Raghu et al. Am Rev Respir Dis 131: 281-289 (1985).*
Border et al. J Clin Invest. 90: 1-7 (1997).*
Border et al. NEJM 331: 1286-1292 (1994).*
Giri et al. Thorax 48: 959-966 (1993).*
Wahl et al. J. Exp. Med. 177: 225-230 (1993).*
Border et al. Kidney Intl. 35(1) 341 (1989).*
Mackay et al J. Clin. Investig. 83: 1160, 1989.*
Connor et al. J. Clin. Investig. 83: 1661, 1989.*
Bassols D. B. C. 263(6): 3039, 1988.*
Flanders et al Biochem 27: 739, 1988.*
Bassols et al., J. Biol. Chem. 263 (6): 3039-3045 (1988).*
Harper et al., Kidney International. 26: 875-880 (1984).*
Flanders et al., Biochemistry 27: 739-746 (1988).*
Webster's Ninth New Collegiate Dictionary, Merriam-Webster Inc., Springfield, MA, 1990, p. 1237.*
Ignotz, R.A. and Massague, J., Tranforming Growth Factor-β Stimulates the Expression of Fibronectin and Collagen and Their Incorporation into the Extracellular Matrix, *J. Biol. Chem.* 261:4337-4345 (1986).
Roberts et al., Transforming Growth Factor Type β: Rapid Induction of Fibrosis and Angiogenesis In Vivo and Stimulation of Collagen Formation In Vitro, *Proc. Natl. Acad. Sci. USA* 83:4167-4171 (1986).
Bassols, A. and Massague, J., Transforming Growth Factor β Regulates the Expression and Structure of Extracellular Matrix Chondroitin/Dermatan Sulfate Proteoglycans, *J. Biol. Chem.* 263:3039-3045 (1988).
Border et al., Transforming Growth Factor β (TGFB) Uniquely Regulates Production and Structure of Glomerular Extracellular Matrix Proteoglycans, *Am. Soc. Nephrol.* Abstract 1287 (1988).
Flanders et al., Antibodies to Peptide Determinants in Transforming Growth Factor β and Their Applications, *Biochemistry* 27:739-746 (1988).
MacKay et al., Transforming Growth Factor-β, *J. Clin. Investigation, Inc.* 83:1160-1167 (1989).
Connor et al., Correlation of Fibrosis and Transforming Growth Factor-β Type 2 Levels in the Eye, *J. Clin. Invest.* 83:1661-1666 (1989).
Chen et al., Transforming Growth Factor Type β Specifically Stimulates Synthesis of Proteoglycan in Human Adult Arterial Smooth Muscle Cells, *Proc. Natl. Acad. Sci. USA* 84:5287-5291 (1987).
Harper et al., *Kidney International* 26:875-880 (1984).
Gressner, A.M., "Liver fibrosis: perspectives in pathobiochemical research and clinical outlook" *Eur. J. Clin. Chem. Clin. Biochem.* 29 (5) :293-311 (1991).
Fausto et al., "Effects of TGF-betas in the liver: cell proliferation and fibrogenesis" *Ciba Found. Symp.* 157:165-74 (1991).
Limper and Roman, "A versatile matrix protein with roles in thoracic development, repair and infection" *Chest* 101(6) :1663-73 (1992).

(Continued)

Primary Examiner—Phillip Gambel
(74) Attorney, Agent, or Firm—McDermott Will & Emery LLP (57) ABSTRACT The present invention provides a method for treating or arresting the progress of pathologies characterized by an accumulation of extracellular matrix components by providing an agent to suppress the activity of transforming growth factor β (TGF-β) a peptide growth factor which is anabolic and leads to fibrosis and angiogenesis. In one embodiment, such agent is anti-TGF-β antibody. Pathologies which can be so treated include, but are not limited to, glomerulonephritis, adult respiratory distress syndrome and cirrhosis of the liver. The invention further provides a method for the diagnosis of pathologies, or incipient pathologies, which are characterized by the accumulation of extracellular matrix components in tissues by determining the levels of TGF-β in the tissues, a high level being indicative of such pathologies.

1 Claim, 11 Drawing Sheets

OTHER PUBLICATIONS

Lissoos and Davis, "Pathogenesis of Hepatic Fibrosis and the Role of Cytokines" *J. Clin. Gastroenterol.* 15(1):64-68 (1992).

Border et al., "Natural inhibitor of transforming growth factor-β protects against scarring in experimental kidney disease" *Nature* 360:361-364 (1992).

Roberts, Anita B. et al. "Transforming Growth Factor Type β: Rapid Induction of Fibrosis and Angiogenesis in vivo and Stimulation of Collagen Formation in vitro." Proc. Natl. Acad. Sci. U.S.A. 83:4167-4171 (1986).

Mustoe, Thomas A. et al. "Acceleratied Healing of Incisional Wounds in Rats Induced by Transforming Growth Factor-β." Science 237:233-1333-1336 (1987).

Quaglino, Daniela Jr. et al. "Transforming Growth Factor-Beta Stimulates Wound Healing and Modulates Extracellular Matrix Gene Expression in Pig Skin: Incisional Wound Model." J. Invest. Derm. 97:34-42 (1991).

Quaglino, Daniela Jr. et al. "Transforming Growth Factor-β Stimulates Wound Healing and Modulates Extracellular Matrix Gene Expression in Pig Skin." Lab. Invest. 63:307-319 (1990).

Sporn, Michael B. et al. "Some Recent Advances in the Chemistry and Biology of Transforming Growth Factor-Beta." J. Cell Biol. 105:1039-1045 (1987).

Border, Wayne A. et al. "Role of TGF-β1 in Experimental Glomerulonephritis." Ciba Foundation Symposium 157:178-193 (1991).

Castilla, Alberto et al. "Transforming Growth Factors β1 and α in Chronic Liver Disease." New England J. Med. 324:933-940 (1991).

Border, Wayne A. and Ruoslahti, Erkki "Transforming Growth Factor-β in Disease: The Dark Side of Tissue Repair." J. Clin. Invest. 90:1-6 (1992).

Okuda, Seiya et al. "Elevated Expression of Transforming Growth Factorβ and Proteoglycan Production in Experimental Glomerulonephritis." J. Clin. Invest. 86:453-462 (1990).

Border, Wayne A. and Ruoslahti, Erkki "Transforming Growth Factor-β in Disease: The Dark Side of Tissue Repair." *J. Clin. Invest.* 90:1-6 (1992).

Sheehan, Dezna C. and Hrapchak, Barbara B. "Carbohydrates." *Theory and practice of Histotechnology.* pp. 159-189 Battelle Press, Columbus (1980).

Border et al., "Transforming Growth Factor β (TGFB) Uniquely Regulates Production and Structure of Glomerular Extracellular Matrix Proteoglycans", *Kidney Intl.* 35(1):341 (1989).

\* cited by examiner

METHODS OF DECREASING THE ACCUMULATION OF EXTRACELLULAR MATRIX ASSOCIATED WITH GLOMERULONEPHRITIS WITH ANTI-TGF-β-SPECIFIC ANTIBODIES

This application is a continuation of application Ser. No. 08/196,892, filed Feb. 14, 1994, now abandoned, which is a continuation of U.S. Ser. No. 07/416,656 filed Oct. 3, 1989, now abandoned; which is a continuation-in-part of U.S. Ser. No. 07/415,081 filed Sep. 29, 1989, now abandoned.

This invention was made with government support under grant numbers CA42507 and CA28896 awarded by the National Institutes of Health and grant number CA30199, a Cancer Center Support grant. Accordingly, the United States government has certain rights in this invention.

BACKGROUND OF INVENTION

This invention relates generally to growth factors and more specifically, to the influence of transforming growth factor-β on excessive extracellular matrix production.

Various pathologies are characterized by a deleterious accumulation of extracellular matrix materials. For example, in progressive glomerular disease, extracellular matrix accumulates in the glomerulus or the glomerular basement membrane, eventually causing end-stage disease and uremia. Similarly, adult respiratory distress syndrome (ARDS) involves the accumulation of matrix materials in the lung while cirrhosis of the liver is characterized by deleterious matrix accumulation in the liver.

Extracellular matrix is a mixture of proteoglycans, glycoproteins and collagens assembled into a complex superstructure. Although a variety of immunologic, hemodynamic and toxic factors have been used experimentally to induce glomerular disease, none of these factors has been shown to directly influence synthesis or degradation of extracellular matrix components. Thus it seems likely that there is another intervening process between acute cell injury and buildup of glomerular extracellular matrix.

There thus exists a need to determine the factors which regulate deleterious accumulation of matrix components in pathological states such as kidney disease. Further, there exists a need to control such agents so as to prevent, limit or treat pathogenic conditions which include inappropriate matrix accumulation. The present invention satisfies these needs and provides related advantages as well.

SUMMARY OF THE INVENTION

The present invention provides a method for treating or arresting the progress of pathologies characterized by an accumulation of extracellular matrix components by providing an agent to suppress the activity of transforming growth factor β (TGF-β) a peptide growth factor which is anabolic and leads to fibrosis and angiogenesis. In one embodiment, such agent is anti-TGF-β antibody. Pathologies which can be so treated include, but are not limited to, glomerulonephritis, adult respiratory distress syndrome and cirrhosis of the liver. The invention further provides a method for the diagnosis of pathologies, or incipient pathologies, which are characterized by the accumulation of extracellular matrix components in tissues by determining the levels of TGF-β in the tissues, a high level being indicative of such pathologies.

BRIEF DESCRIPTION OF THE DRAWINGS

FIG. 1 shows an analysis of dose response effects of TGF-β on proteoglycan production by SDS-PAGE. Cultures of rat mesangial cells were treated with TGF-β for 48 hours and metabolically labeled with $^{35}S$ sulfate. Equal volumes of conditioned media were analyzed by SDS-PAGE and fluorography. Beginning at 0.25 ng/ml (lane 2) there is an increase in PG I and PG II bands. At 2.5 ng/ml (lane 4) a shift in electrophoretic mobility is seen and at higher concentrations of 75 and 150 ng/ml (lanes 7 and 8) an inhibitory effect is present. Lane 1 is control and lanes 2–8 represent TGF-β at 0.25, 0.75, 2.5, 25, 75 and 150 ng/ml.

FIG. 3 shows effects of growth of factors on proteoglycan production. Cultures of rat mesangial cells were treated with growth factors for 48 hours and metabolically labeled with $^{35}S$ sulfate. Equal volumes of conditioned media were analyzed by SDS-PAGE and fluorography. TGF-β increased two broad bands centered at 220 kD (biglycan) and 120 kD (decorin) and induced a structural change detected as a shift in electrophoretic mobility. PDGF, IL-1 and TNF had no significant effects.

FIG. 4 shows the effect of PDGF on the increased proteoglycan synthesis induced by TGF-β. Equal volumes of media from cultures labeled with $^{35}S$ sulfate and treated with various growth factor combinations were analyzed by SDS-PAGE and fluorography. (Lane 1: control; Lane 2: TGF-β, 25 ng/ml; Lane 3: TGF-β 25 ng/ml+PDGF, 1 U/ml; Lane 4: TGF-β 25 ng/ml+PDGF, 0.5 U/ml).

FIG. 5 shows the immunological identification of proteoglycans affected by TGF-β. Equal volumes of control (lanes 1 and 3) or TGF-β treated (lanes 2 and 4) conditioned media were immunoprecipitated with antiserum to synthetic peptides of the human core proteins of biglycan (lanes 1 and 2) and decorin (lanes 3 and 4). TGF-β specifically increased the biglycan and decorin bands (lanes 2 and 4) compared to control.

FIG. 6 shows the characterization of the proteoglycans regulated by TGF-β. Metabolically labeled conditioned media were subjected to specific enzyme digestion. Lanes 1–4 are control and 5–8 are media from TGF-β treated cultures (25 ng/ml). Lanes were treated with: saline (1 and 5), heparinase (2 and 6), chondroitinase ABC (3 and 7) and chondroitinase AC (4 and 8). The bands were digested in lanes 3 and 7 indicating the presence of a chondroitin/dermatan sulfate proteoglycan. Note the appearance of a core protein band (lane 7) which has been increased by TGF-β.

FIG. 7 shows the extracellular matrix in experimental glomerulonephritis. The percent of glomerular area occupied by extracellular matrix was semiquantitated during the course of glomerulonephritis induced by injection of anti-thymocyte serum (n=30 glomeruli scored in each of 6 animals at each time point). *p<0.001 **p<0.01 nephritic animals compared to normal control. Values are mean±SD.

FIG. 8 shows the glomerular ultrastructure in experimental glomerulonephritis. Electron micrographs showing area of normal mesangial matrix (A) in a control animal and an area of increased mesangial matrix (B) in an animal on day 14 of glomerulonephritis induced by injection of anti-thymocyte serum (×6,000).

FIG. 9 shows proteoglycan production by cultured glomeruli. Equal numbers of glomeruli isolated from animals (n=2 at each time point) on day 0 (control) or 1, 4, 7, 14 and 28 days after injection of anti-thymocyte serum were cultured for 24 hours and biosynthetically labeled with $^{35}S$ sulfate. Conditioned media was analyzed by SDS-PAGE with fluorography. Compared to day 0, there was a 17-fold increase in biglycan and decorin production on day 4, a 49-fold increase on day 7, a 20-fold increase on day 14 and a 5-fold increase on day 28.

FIG. 12 shows the specificity of the blocking effect of the anti-TGF-β antibody. Conditioned media from nephritic glomeruli on day 7 following anti-thymocyte serum injection were mixed with normal preimmune serum (NS), anti-TGF-β antibody (AB), or immunizing peptide (P) plus antibody. The peptide abolished the ability of the antibody to block the stimulation of proteoglycan production.

FIG. 14 shows the immunological identification of the proteoglycans from the conditioned media shown in FIG. 13. Equal volumes of conditioned media from control or nephritic glomeruli were immunoprecipitated with antiserum to synthetic peptides of the human core protein of biglycan (lanes 1 and 2) and decorin (lanes 3 and 4). The biglycan (lane 2) and decorin (lane 4) bands were specifically increased in the conditioned media from the nephritic glomeruli (lanes 2 and 4) compared to control (lanes 1 and 3).

FIG. 15 shows the expression of TGF-β in the kidney. Glomerular cells synthesizing TGF-β after injection of anti-thymocyte serum were detected by immunofluorescence (n=30 glomeruli counted in each of 6 animals at each time point). *p<0.001 nephritic animals compared to normal control. Values are mean±SD.

FIG. 17 shows micrographs showing the enlargement of glomeruli in nephritic kidneys. Kidneys from rats made nephritic by an injection of anti-thymocyte serum and examined on day 14 after the injection. Panel A is from a rat that received normal rabbit serum injections four successive days, starting on the day of the anti-thymocyte serum injection. Panel B is from a rat that received rabbit anti-TGF-β under a similar regimen. Toluidine blue staining. X500 magnification

DETAILED DESCRIPTION OF THE INVENTION

The invention provides a method of inhibiting the accumulation of extracellular matrix in a tissue by suppressing the activity of TGF-β in the tissue. Also provided is a method for treating pathologies characterized by an accumulation of extracellular matrix in a tissue by suppressing the activity of TGF-β. TGF-β is responsible for the increased synthesis of extracellular matrix observed in various pathologies, such as glomerulonephritis, adult respiratory distress syndrome and cirrhosis of the liver.

A variety of growth factors have been suggested to play a role in extracellular matrix production. However, their influence on the pathological accumulation of matrix components has been unclear. The invention is predicated on the new discovery that tissues prone to pathological accumulation of matrix synthesize particular proteoglycans. Agents which inhibit TGF-β activity, such as antibodies reactive with TGF-β, have been found to block the stimulatory effect of TFG-β on proteoglycan production. In this respect, TGF-β is unique among growth factors tested, and thus manipulating this specific effect of TGF-β has utility in controlling or treating the inappropriate and undesirable accumulation of matrix components in various pathologies.

Mesangial cells are one of the cell types that make up kidney glomerulus. In the normal glomerulus, the mesangial cells are surrounded by extracellular matrix. An increase in the quantity of mesangial matrix, with or without mesangial hypercellularity, is the earliest histologic finding in many forms of glomerulonephritis and in diabetic nephropathy. Cultured mesangial cells are known to secrete several matrix components including proteoglycans, fibronectin, laminin, entactin, thrombospondin and collagen types I, III, IV and V. However, the exact composition and supramolecular organization of the mesangial matrix, as well as the factors that control its synthesis assembly and degradation, have been unknown.

To study factors controlling the composition of the mesangial matrix, mesangial cells in culture were treated with IL-1, PDGF, TNF and TGF-β. Analysis of the culture media indicated that TGF-β increased the amount of two components, identified as the proteoglycans biglycan and decorin. PDGF, IL-1, and TNF had no significant effect over the control.

Glomerulonephritis can be induced by specific immunological injury to the mesangial cell. Glomeruli isolated show increased biglycan and decorin production. Moreover, conditioned media from cultured nephritic mesangial cells stimulate biglycan and decorin synthesis by normal mesangial cells. An equivalent stimulatory effect can be produced by the addition of exogenous TGF-β. Moreover, agents which can block the effect of TGF-β, such as an antiserum, block the stimulatory effect of exogenous TGF-β. Such agents, including monoclonal or polyclonal antibodies, PDGF and Arg-Gly-Asp containing peptides, can be used to specifically control or treat deleterious matrix proteoglycan synthesis. Thus, such agents can be used to prevent any condition associated with extracellular matrix accumulation, for example scarring, or to treat pathologies characterized by an accumulation of extracellular matrix in a tissue by contacting the tissue with an agent which suppresses TGF-β activity. The pathologies capable of treatment are characterized by an accumulation of extracellular matrix and include glomerulonephritis, adult respiratory distress syndrome and cirrhosis of the liver. However, these pathologies are merely representative and a person skilled in the art would readily recognize the method to be useful in any pathology associated with accumulation of extracellular matrix.

The presence of elevated levels of TGF-β can be used diagnostically to determine the presence or incipient presence of pathologies deriving from extracellular matrix accumulation. For example, immunoassays utilizing anti-TGF-β antibodies provide such a diagnostic test. Various formats of such assays are available and well known to those skilled in the art, including RIA, ELISA and immunofluorescence. See generally, Ruoslahti et al., M. Enz., 82:803–831 (1982) which is incorporated by reference herein. Alternatively, nucleic acid probes can be used to detect and quantitate TGF-β mRNA for the same purpose. Such methods are also well known in the art.

Additionally, a method of decreasing the production of a proteoglycan by a cell which produces a proteoglycan is provided. The method comprises decreasing the amount of TGF-β to which the cell is exposed. Such amount of TGF-βcan readily be ascertained, i.e. an amount under that present in a normal cell leading to decreased proteoglycan production. Alternatively, the cellular production of a proteoglycan can be decreased by inhibiting the proteoglycan producing activity of TGF-β. This inhibition can be performed by the methods taught in this invention, for example, binding TGF-β with a ligand. Additionally, it is recognized that certain modifications or amino acid substitutions can be performed on TGF-β without changing its essential function. Thus, by "TGF-β" is meant all modifications to TGF-β as long as the essential function of increasing extracellular matrix production is maintained. TGF-β1 and TGF-β2 are both known to exhibit this function, see for example Ignotz and Massague, J. Biol. Chem. 261:4337–4345 (1986) and Bassols and Massague, J. Biol. Chem. 263:3083–3095 (1986) both of which are incorporated by reference herein.

The following examples are intended to illustrate but not limit the invention.

EXAMPLE I

Effect of TGF-β on Mesangial Cell Culture

Mesangial cells were obtained from intact glomeruli of 4 to 6 week old Sprague-Dawley rats according to the method of Harper, et al., Kidney International 26:875 (1984), which is incorporated herein by reference. The growth medium used was RPMI 1640 (Cell-Gro, Washington, D.C.) supplemented with 20% heat-inactivated fetal calf serum (FCS) (Hyclone, Logan, Utah), 50 U/ml penicillin, 100 µg/ml streptomycin, 0.66 U/ml insulin, and 300 mg/ml L-glutamine. Between day 15 to 20, primary cultures were detached with a solution of 0.025% trypsin—0.5 mM EDTA (Flow Labs, McLean, Va.) and $2\times10^6$ cells were added to flasks. The cells were passed every 7 days and all experiments were performed on cells between passages 3 and 7.

Phase contrast and immunofluorescence microscopy was performed by growing cells to subconfluence on coverslips in plastic wells. The cells were fixed with 3.7% paraformaldehyde for 10 minutes at 22° C. After washing with phosphate buffered saline (PBS), the cells were incubated with specific antibodies and washed and reincubated with FITC-anti-rabbit IgG. The coverslips were mounted and examined by phase contrast and immunofluorescence microscopy. This technique revealed a homogeneous population of cells that were identified as mesangial cells according to the following findings: 1) presence of spindle shaped morphology, 2) absence of polygonal-shaped cells, 3) bright immunofluorescence staining for myosin, actin, desmin, and anti-thy 1.1 antibody and negative staining for common leukocyte antigen, cytokeratin and factor VIII. The cells also showed no morphologic evidence of toxicity upon exposure to aminonucleoside of puromycin (Sigma, St. Louis, Mo.).

To study proteoglycan synthesis, equal numbers of cells were added to 6-well multiwell plates or petri dishes and allowed to grow to subconfluence. Cultures were made serum free for 24 hours to arrest cell proliferation. The cell layers were washed 3 times with sterile PBS and serum and antibiotic free RPMI was added as a low sulfate growth medium for $^{35}S$ methionine labeling. The following growth factors were added to the media for 48 hours: TGF-β, bovine or porcine (R&D Systems, Inc., Minneapolis, Minn.) human PBGF (Collaborative Research, Inc., Bedford, Mass.) human recombinant IL-1 α (Collaborative Research, Inc. Bedford, Mass.) and recombinant human TNF (Amgen, Thousand Oaks, Calif.). The concentrations chosen were: TGF-β (25 ng/ml), PDGF (10 U/ml), IL-1 (5 U/ml) and TNF (500 U/ml). Eighteen hours prior to termination of the experiment, $^{35}S$ methionine (150 µCi/ml), to label proteins, or $^{35}S$ sulfate (200 µCi/ml), to label proteoglycans, were added to the cultures. Isotopes were obtained from New England Nuclear (Boston, Mass.). The culture media were removed, phenylmethylsulfonyl fluoride (PMSF), pepstatin and aprotinin (Sigma, St. Louis, Mo.) were added to protease inhibitors, and the mixtures were centrifuged for 20 minutes to remove debris. The remaining cell monolayers were removed by washing 2 times with PBS followed by incubation with 300 µl of SDS-PAGE sample buffer. The layers were detached by agitation. Samples were electrophoresed immediately and the remainder stored at −20° C.

The uptake of $^3H$-thymidine as a marker of cell proliferation was evaluated by the addition of 10 µl per well of a 1 mCi/ml solution of $^3H$-thymidine (84 curies/µMol) diluted 1:100 with sterile PBS. The incubations were carried out for 24 or 48 hours after which the cells were harvested onto glass fiber filter mats using a cell harvester (Skatron, Lierbyen, Norway). Prior to harvesting the cells, the media was aspirated and the cells were washed twice with Hank's balanced salt solution. Incorporation of $^3H$-thymidine into cellular DNA was measured by counting the filter mats in a liquid scintillation counter (Beckman, Irvine, Calif.). In separate experiments aliquots of cells were counted visually in a hemacytometer to verify that the incorporation of $^3$H-thymidine paralleled changes in cell numbers. Prior to harvesting, cells were evaluated for evidence of cytotoxicity by phase microscopy. Cell viability was also assessed by Trypan blue exclusion.

Figure 1:
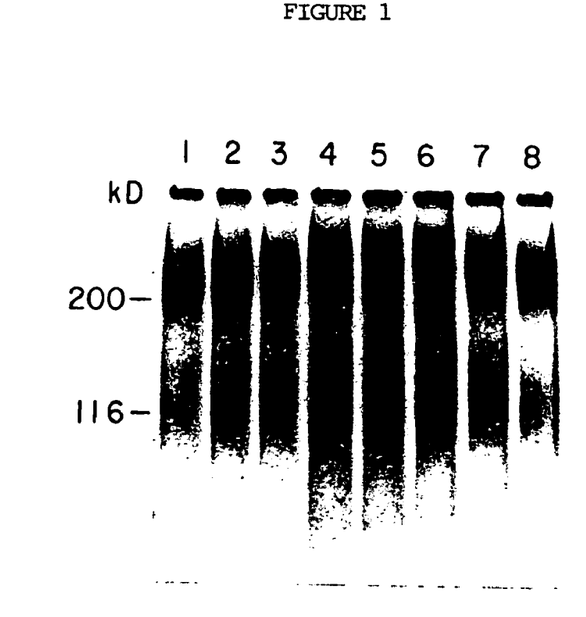
Figure 2:
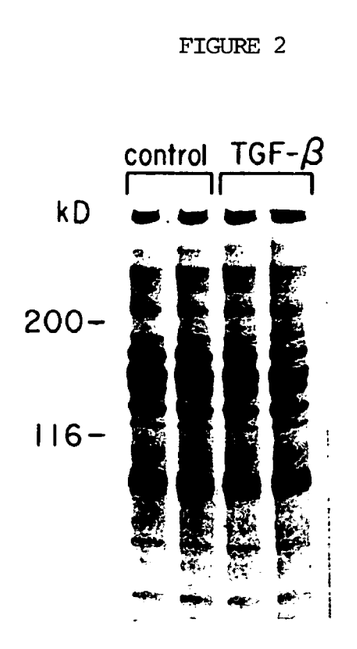
FIG. 2 shows the effect of TGF-β on synthesis of proteins secreted by mesangial cells. Cultures of rat mesangial cells were treated with TGF-β for 48 hours and metabolically labeled with $^{35}S$ methionine. Equal volumes of conditioned media were analyzed by SDS-PAGE and fluorography. TGF-β did not affect the general pattern of secreted proteins.
Figure 3:
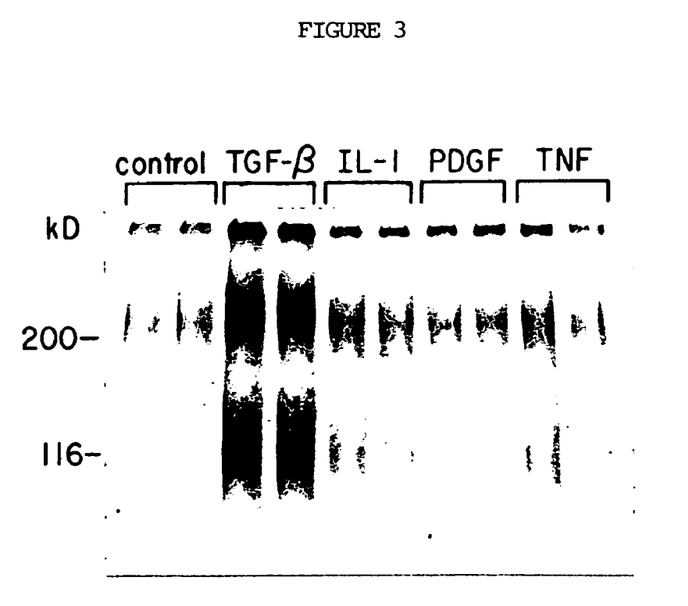

The biosynthetic labeling of cultured mesangial cells with $^{35}$S sulfate, to label proteoglycans, and $^{35}$S methionine, to label proteins, showed that the addition of TGF-β induced a dramatic increase in the production of proteoglycans. Under control conditions, the mesangial cells secreted into the medium two distinct small proteoglycans that were identified as broad bands on SDS-PAGE, centered at 220 and 120 kD (FIG. 1). In addition, there was some labeled material that did not enter the gel. The intensity of each of these bands was increased by the TGF-β treatment and the bands stopped at a slightly higher molecular weight. The maximal effect of TGF-β occurred at 25 ng/ml where there was an 8 to 10 fold increase in proteoglycan production compared to control levels. At higher concentrations there was a decrease in the action of TGF-β with the effects on proteoglycan production disappearing at 150 ng/ml. Examination of proteoglycan incorporation into the extracellular matrix by extraction and parallel analysis of the cell layer, showed a qualitatively identical TGF-β effect. However, the bands were considerably less intense indicating that the proteoglycans were mostly secreted into the medium. Under the experimental conditions employed, no demonstrable effect on the pattern of protein synthesis was observed, as revealed by $^{35}$S methionine labeling followed by SDS-PAGE (FIG. 2) and analysis of the gels by laser densitometry. None of the other growth factors, PGDF, IL-1 or TNF, caused induction of proteoglycans similar to TGF-β (FIG. 3).

Figure 4:
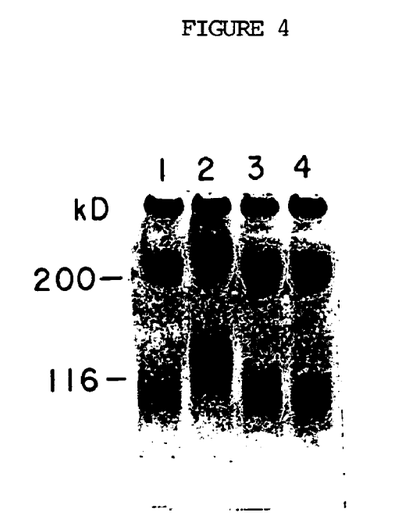

In order to study potential growth factor interactions, mesangial cells were exposed to IL-1, PDGF and TNF before adding TGF-β as described above. None of these three growth factors alone altered proteoglycan production. PDGF, however, when added to the cells before TGF-β, blocked the expected increase in proteoglycan production (FIG. 4). The blocking effect did not occur with IL-1 or TNF. The peptide GRGDSP also blocked the increased proteoglycan synthesis caused by the addition of TGF-β to the mesangial cell cultures, whereas peptide GRGESP did not (Pierschbacher and Ruoslahti, Nature 309:30–33 (1984), which is incorporated herein by reference).

EXAMPLE II

Identification of Proteoglycan Species

1. Immunoprecipitation

Immunoprecipitations were performed by adding 100 μl of antiserum to 500 μl of conditioned medium or 300 μl of cell extract collected from duplicate wells in the presence or absence of added growth factors. In duplicate wells, cells were detached and counted to ensure uniformity of cell number. Preimmune serum was used in parallel control experiments. The samples were incubated overnight at 4° C. with mixing in 4 ml conical tubes precoated with bovine serum albumin (BSA). Protein-A-Sepharose beads (Sigma, St. Louis, Mo.) were preincubated with fresh RPMI for 60 minutes at 22° C. To precipitate the antigen-antibody complexes, 50 μl of suspended protein-A-Sepharose was added to the samples, and mixed at 4° C. for 120 minutes. The samples were centrifuged for 10 minutes at 2000×G and the supernatant removed. The pellets were washed 10 times with 1 ml of ice cold PBS containing 0.5 M NaCl, 0.1% Triton X-100 pH 7.4. Finally, the pellets were washed with ice cold PBS, transferred to new tubes, recentrifuged, and washed 3 times with PBS. The pellets were dissolved in 40 μl of SDS-PAGE sample buffer containing 3% SDS and 10% β mercaptoethanol (Sigma, St. Louis, Mo.) and boiled for 5 minutes.

Figure 5:
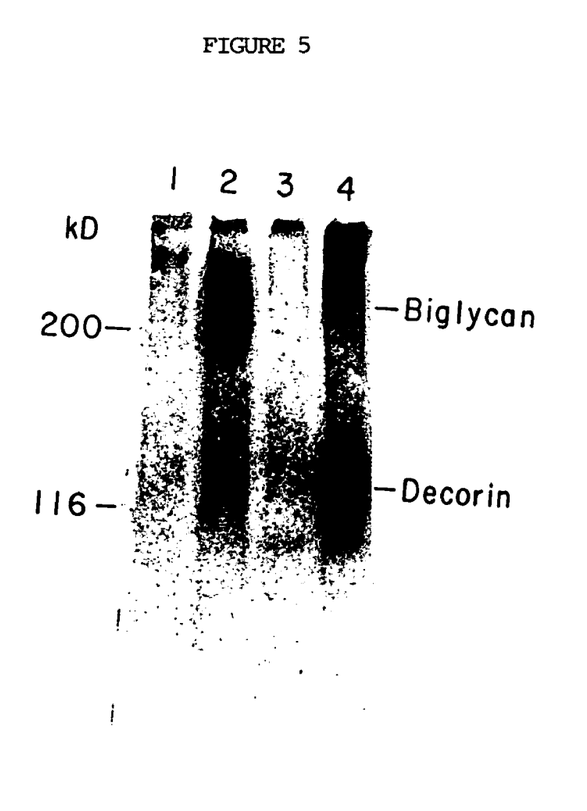

The molecular size and type of the two proteoglycans produced by mesangial cells and regulated by TGF-β, corresponded to that of two proteoglycans, biglycan (PG I) and decorin (PG II). These proteoglycans are known to have 45 kD core proteins, the sequences of which have been deduced from cDNA (Krusius, T and Ruoslahti, E., Proc. Natl. Acad. Sci., USA 83:7683–7687 (1986) and Fisher et al., J. Biol. Chem. 264:4571–4576 (1989) which are incorporated herein by reference). Polyclonal antibodies produced to synthetic peptides from the N-terminal sequences of these proteoglycans were used to identify the proteoglycans in the mesangial cell culture media. Immunoprecipitation of $^{35}$S sulfate labeled conditioned media from control and TGF-β treated cells followed by SDS-PAGE identified the 220 kD band as biglycan and the 120 kD band as decorin (FIG. 5). Immunoprecipitation of conditioned media from $^{35}$S methionine-labeled cells with anti-fibronectin, laminin and type IV collagen antibodies and SDS-PAGE analysis of the immunoprecipitates showed no visible effect of TGF-β on the levels of these proteins (data not shown).

2. Enzyme Digestion

Digestion with glycosaminoglycan-degrading enzymes was used to determine the type of proteoglycans that were regulated by TGF-β. The digestion was performed on conditioned media after biosynthetic labeling. Aliquots of medium (25 μl) were mixed with 100 milliunits of chondroitinase ABC or chondroitinase AC both in 100 mM Tris-HCl, pH 7.5, 10 mM calcium acetate, 2 mg/ml BSA or 100 milliunits of heparinase II in 50 mM Tris-HCl, pH 7.4, 1 mM calcium chloride, 5 mM calcium acetate. All samples also received 1 mM PMSF, 5 mM benzamidine, 100 μg/ml soy bean trypsin inhibitor, 10 μg/ml leupeptin and 10 μg/ml antipain. All materials were obtained from Sigma. Chondroitinase-containing mixtures were incubated at 37° C. for 1.5 hours. At termination samples were prepared for SDS-PAGE.

Figure 6:
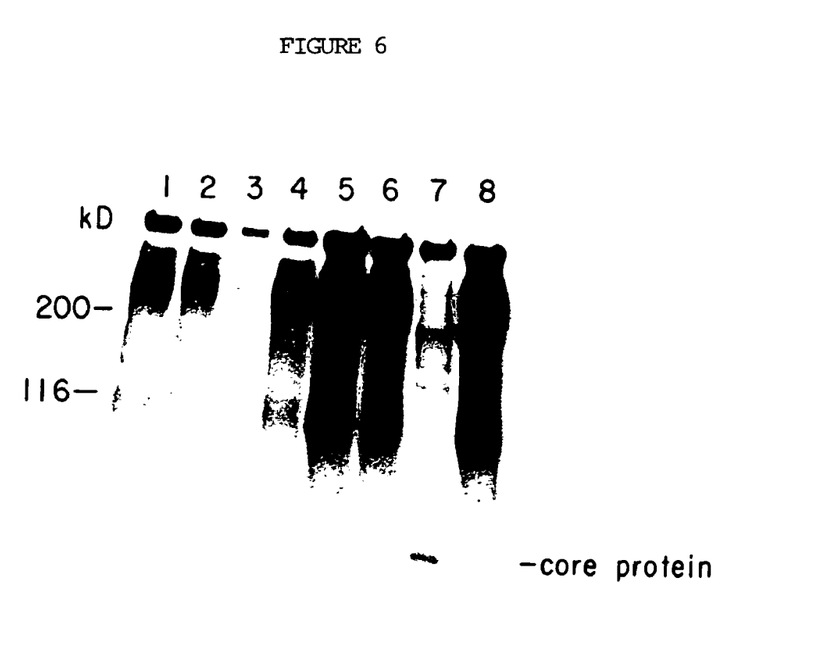

The small proteoglycans from control and TGF-β treated cells were degraded by chondroitinase ABC but were insensitive to chondroitinase AC and heparinase (FIG. 6). The labeled material (large proteoglycan(s)) at the top of the gel appeared to be partially sensitive to digestion with both chondroitinase ABC and heparinase. These results indicate that the major proteoglycans produced by mesangial cells are chondroitin/dermatan sulfate proteoglycans. In addition to identifying the glycosaminoglycan type, incubation of TGF-β conditioned medium with chondroitinase ABC resulted in the appearance of a new 45 kD band (FIG. 6). This band is likely to represent the proteoglycan core proteins after removal of portions of the chondroitin/dermatan sulfate chains. Enzyme treatment of conditioned medium from control cells did not yield a visible core protein. This indicates that part of the regulatory action of TGF-β is to stimulate new synthesis of the proteoglycan core proteins.

EXAMPLE III

Induction of Experimental Glomerulonephritis, Histologic Examination, Preparation of Glomerular Cultures, Culture Media and Antibody Production a. Induction of Experimental Glomerulonephritis To study the role of TGF-β in the glomerular proteoglycan synthesis in vivo, a glomerulonephritis model in which the disease is induced with an anti-thymocyte serum (ATS) was produced by immunizing New Zealand white rabbits with $1 \times 10^6$ rat thymocytes in complete Freund's adjuvant, followed by boosting with $1 \times 10^6$ thymocytes given intravenously two and four weeks later. Preimmunization serum was collected from the same animal and used in control experiments as normal rabbit serum. Prior to use, ATS and normal serum were absorbed 3 times each with packed rat erythrocytes and rat liver powder. The serum was then heat inactivated at 56° C. for 30 minutes. Glomerulonephritis was induced in Sprague Dawley rats (4–6 weeks old) by intravenous administration of 1 ml ATS per 100 g body weight and 1 ml normal rabbit serum as a source of complement. Control animals received an equal volume of normal serum instead of ATS. Animals were sacrificed on days 1,4,7,14 and 28 following ATS administration for histologic examination of kidney tissue and isolation of glomeruli for culture. On the day of sacrifice, systolic blood pressure was measured in the conscious state with a tail-cuff sphygmomanometer (Narco Biosystems, Houston, Tex.) connected to a recorder (Pharmacia, Uppsala, Sweden) and serum creatinine determined by using Sigma Diagnostics Creatinine reagents (Sigma, St. Louis, Mo.). Animals were housed in the metabolic cages and total urine output was collected daily during the first week and weekly thereafter for measurement of 24-hour protein excretion by sulfosalicylic acid precipitation according to the method of Border, et al., Kidney International 8:140 (1975), which is incorporated herein.

b. Histologic Examination

Kidney tissue from each animal was processed and examined by light, immunofluorescence and electron microscopy as described in Border, et al., Kidney Int. 8:140–148 (1975), which is incorporated herein by reference. For light microscopy, tissues were fixed neutral formalin, embedded in paraffin and 2μ sections stained with periodic acid-Schiff. To quantitate mesangial matrix and glomerular cellularity, all sections were coded and read by an observer of the experimental protocol applied. Thirty glomeruli (80–100 μm in diameter) were selected at random and cell nuclei counted and the degree of glomerular matrix expansion determined using a published method (Raij, et al., Kidney Int. 26:137–143 (1984), which is incorporated herein by reference). The percentage of each glomerulus occupied by mesangial matrix was estimated and assigned a score beginning with 1=0 to 25%, 2=25 to 50%, 3=50 to 75% and 4=75 to 100%.

Immunofluorescence microscopy was performed on tissue snap-frozen in liquid nitrogen, fixed in acetone, and 4 μm sections stained with fluorescein isothiocyanate-conjugated antisera (Cooper Biomedical, Malvern, Pa.) to rabbit and at IgG and C3. For electron microscopy, tissue was placed in Karnovsky's fixative at 4° C. overnight, embedded in Epon and ultrathin sections stained with uranyl acetate and lead citrate.

Figure 7:
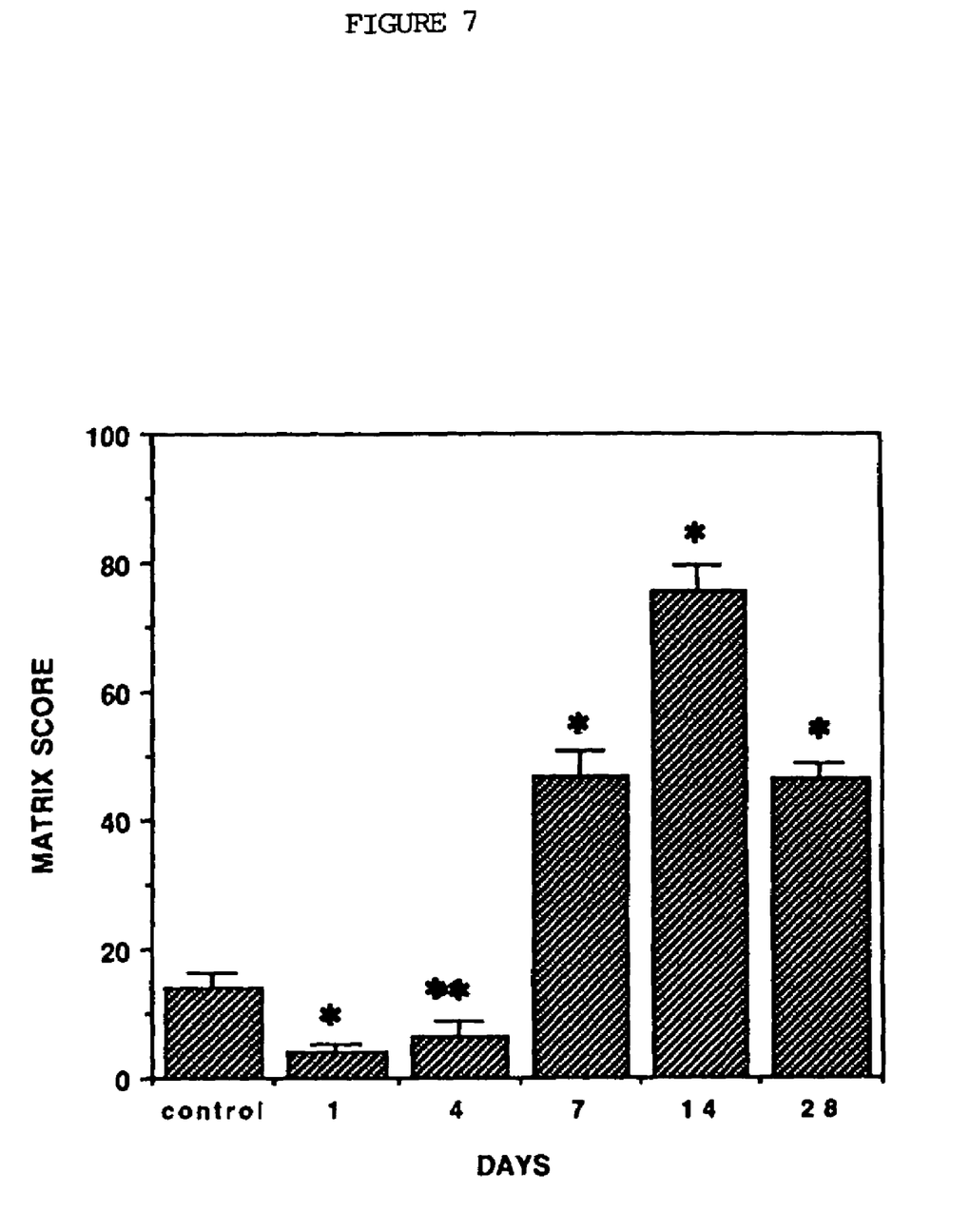
Figure 8A:
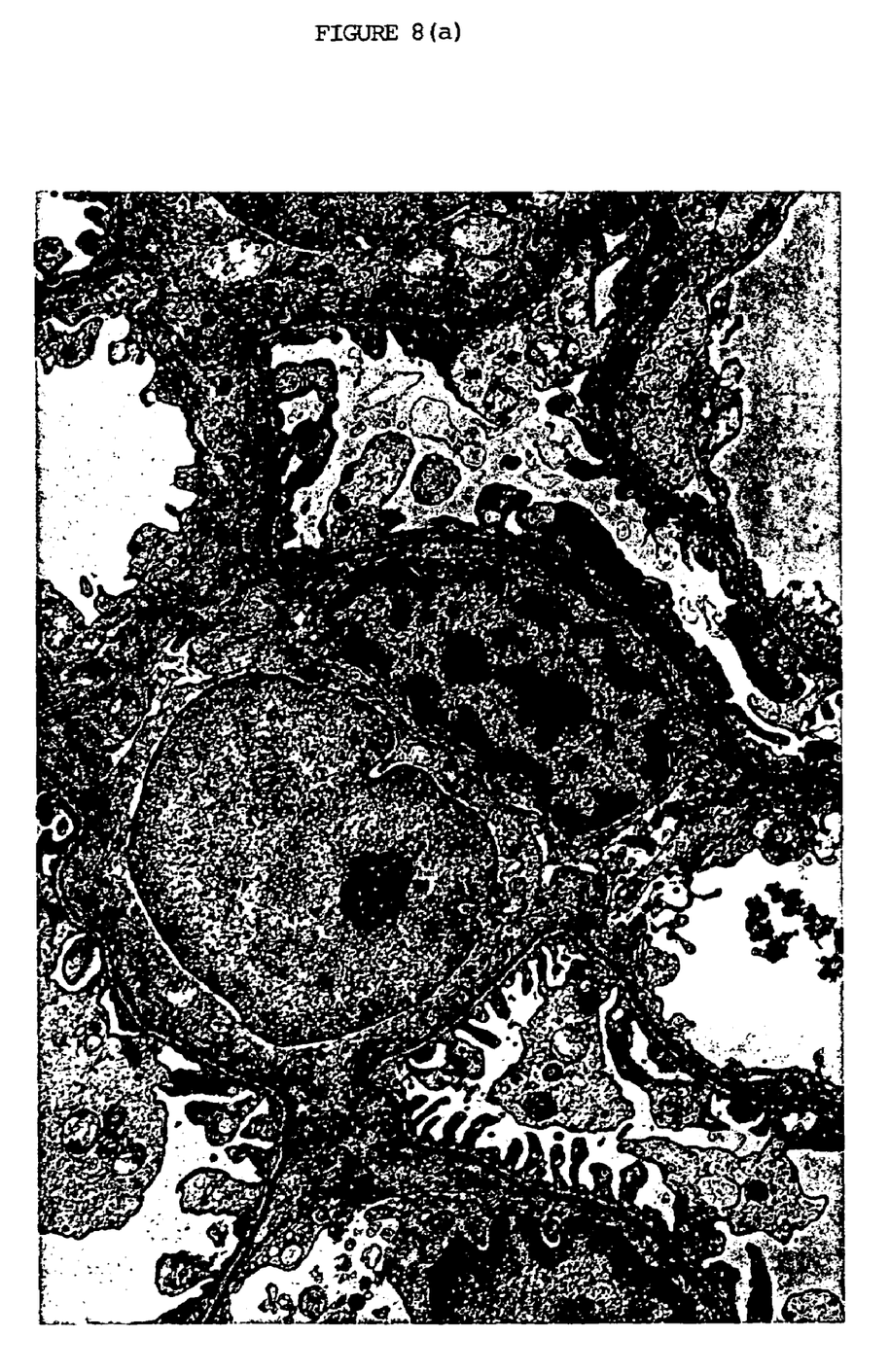
Figure 8B:
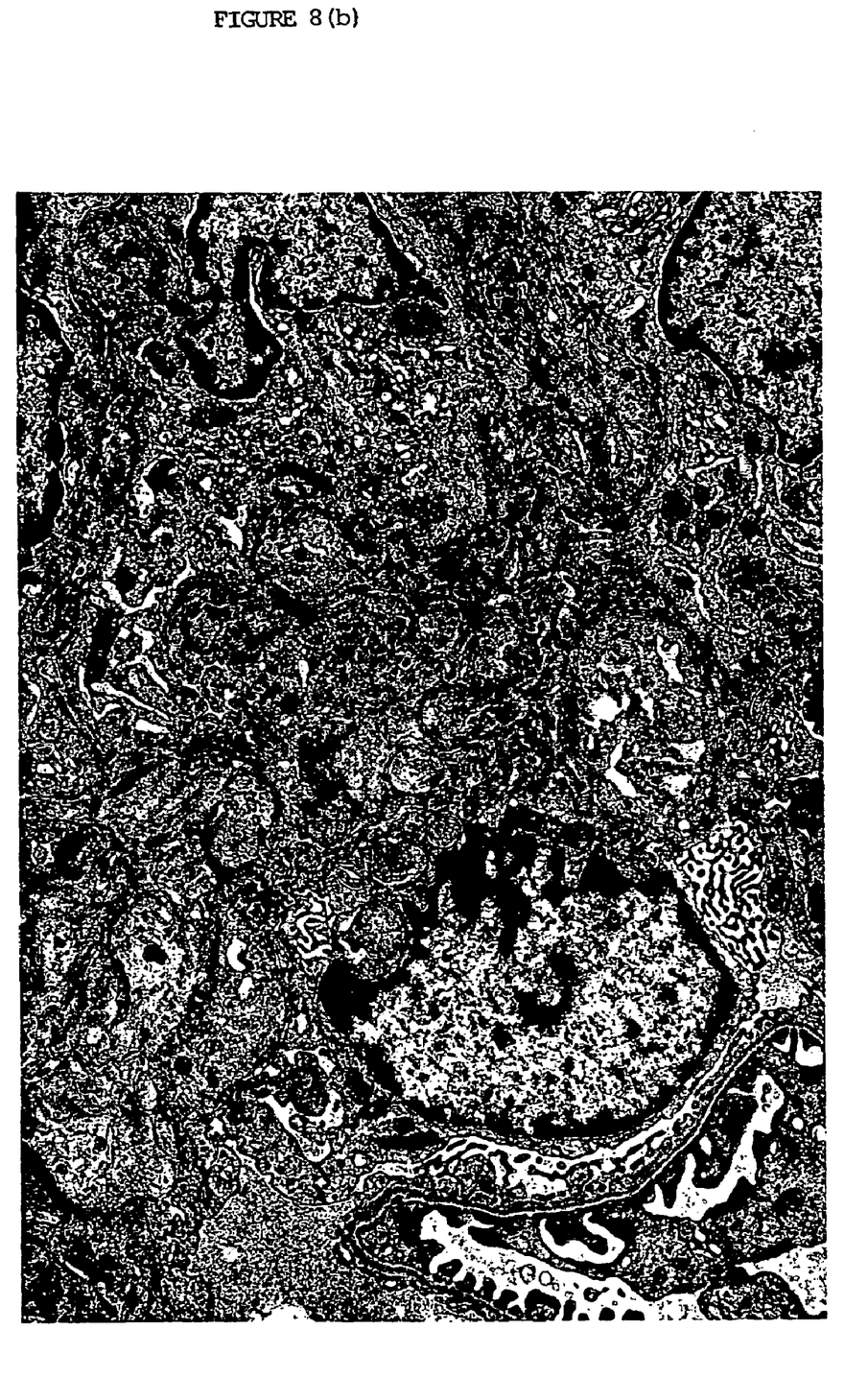

The dose of ATS administered produced an acute form of mesangial injury glomerulonephritis. There was a definite increase in the mesangial extracellular matrix, beginning on day 7, becoming maximal on day 14, and decreasing thereafter (FIG. 7). The decrease in matrix noted on days 1 and 4 coincided with a decrease in glomerular cellularity due to complement-mediated lysis of a portion of the mesangial cells. Ultrastructural examination confirmed the increase in mesangial matrix (FIG. 8). Functional changes in this model of glomerulonephritis consisted of: 1) transient proteinuria during the first week, 2) no significant change in levels of serum creatinine and, 3) a slight but significant elevation of systolic blood pressure only on day 14 in the nephritic group.

c. Glomerular Culture

Rats were anesthetized intramuscularly with ketamine HCl, 10 mg/100 g body weight, and xylazine 0.5 mg/100 g body weight. The kidneys were perfused in situ via the aorta with phosphate buffered solution (PBS) (pH 7.4), and then excised. The capsules were removed and the cortical tissue dissected out and minced with a razor blade. Glomeruli were isolated using the graded sieving technique (Striker et al, 1985). A spatula was used to pass minced cortex through a 149 μm nylon screen (Spectrum, Los Angeles, Calif.). The tissue which emerged was passed sequentially through a 105 μm and 74 μm sieve. Intact glomeruli retained on the 74 μm sieve were removed, and washed three times in PBS, pH 7.4 and resuspended at $5 \times 10^3$ glomeruli per ml in serum-free and antibiotic-free RPMI 1640 (Cell-Gro, Washington, D.C.) in 6-well multiwell plates. After 24 hours of incubation, the cultures were biosynthetically labeled by addition of 200 μCi/ml of $^{35}S$ sulfate for an additional 24 hours. All isotopes were obtained from New England Nuclear (Boston, Mass.). The culture media were removed, phenylmethylsulfonyl fluoride, peptain and aprotinin (Sigma, St. Louis, Mo.) were added as protease inhibitors, and the mixtures centrifuged for 20 minutes to remove cellular debris. Samples were electrophoresed immediately and the remainder stored at –20° C.

d. Preparation of Conditioned Media From Glomerular Cultures

Media conditioned by exposure to normal ATS glomeruli for 48 hours was collected. In order to activate precursor TGF-β, aliquots of the conditioned media were acidified to pH 3.2 for 1 hour by addition of 1N HCl. The transiently acidified media was brought to pH 7.4 with 1N NaOH and dialyzed against serum-free RPMI for 24 hours at 4° C. In some experiments 100 μl of antiserum made against a synthetic peptide from TGF-β was added to 1 ml of activated conditioned media and incubated overnight at 4° C. with continuous mixing. To determine the specificity of the TGF-β antiserum, 100 μg of synthetic peptide that had been used for the immunization was added to 1 ml of antiserum and incubated for 2 hours at 22° C. with continuous mixing. Prior to addition to mesangial cell cultures, all conditioned media were centrifuged 1000×G for 20 minutes and passed through a 0.2 μm Uniflo filter (Schleicher & Schell, Inc., Keene, N.H.).

e. Anti-TGF-β Antibodies

The anti-TGF-β antiserum was prepared against a synthetic peptide from residues 78–109 of the human mature TGF-β. A partial amino-acid sequence of the human mature form of TGF-β is described in Derynck et al., Nature 316:701 (1985) which is incorporated by reference herein. Antisera raised against the same peptide, whose terminal cysteine residues were disulfide-linked, have previously been shown to inhibit the binding of TGF-β to its receptors (Flanders et al., Biochemistry 27:739 (1988), which is incorporated herein by reference). The peptide was synthesized in an Applied Biosystems solid phase peptide synthesizer and purified by HPLC. A rabbit was immunized with 2 mg per injection of the peptide mixed with 0.5 mg of methylated BSA (Benoit et al., Proc. Natl. Acad. Sci. USA 79:917 (1982), which is incorporated herein by reference) and emulsified in Freund's complete adjuvant. The injections were generally given four weeks apart and the rabbit was bled approximately a week after the second and every successive, injection. The bleedings used in this work had a titer (50% binding) of about 1:3,000 to about 1:30,000 in radio immunoassay, bound to TGF-β1 in immunoblots and inhibited the induction of proteoglycan synthesis caused by TGF-β1 in cultured mesangial cells. Further, it is expected that the antibodies would also inhibit TGF-$\beta_2$. Additionally, the antibody has an affinity of about $10^8$ or greater as measured by radio immunoassay and calculated as described in Muller, J. Imm. Met. 34:345–352 (1980). Preferably the antibody has an affinity of 109 or greater. A second polyclonal antibody (anti-LC) made against a synthetic peptide corresponding to the $NH_2$-terminal 30 amino acids of mature TGF-β, as described in Flanders et al., J. Cell Biol. 108: 653–660 (1989), which is incorporated herein by reference, stains intracellular TGF-β.

EXAMPLE IV

Glomerular Proteoglycan Production and TGF-β

Figure 9:
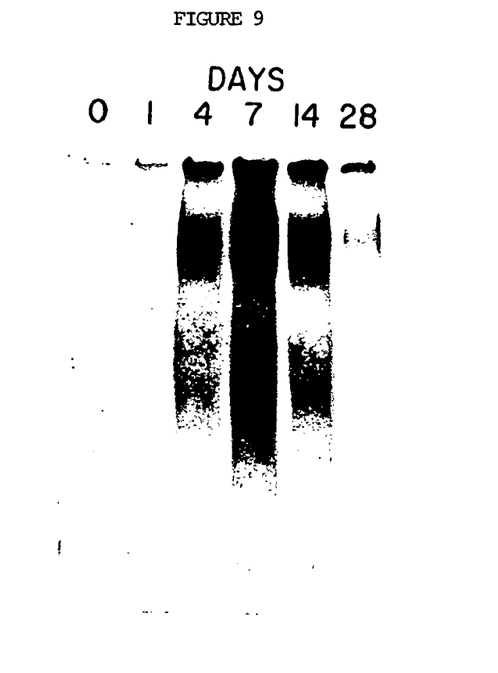
Figure 10:
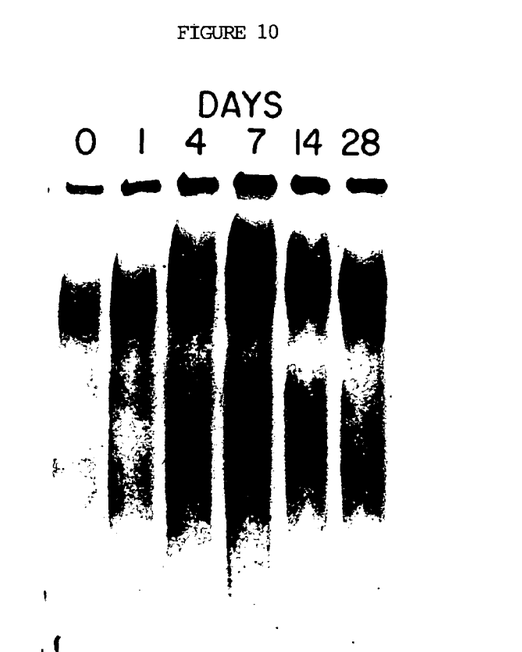
FIG. 10 shows the effect of conditioned media from nephritic glomeruli on proteoglycan production by normal cultured mesangial cells. The cells were biosynthetically labeled and the conditioned media analyzed by SDS-PAGE with fluorography. The conditioned media from nephritic glomeruli stimulated the production of biglycan and decorin beginning on day 1, peaking on day 7 and then production decreased toward control levels by day 28.

Groups of nephritic animals were sacrificed 1, 4, 7, 14 and 28 days after being injected with ATS. Their glomeruli were isolated, placed in culture, and biosynthetically labeled to identify newly synthesized proteoglycans. One day after ATS injection, proteoglycan synthesis was the same as in normal controls; however, on day 4 there was a striking induction of proteoglycan production, that reached a 49-fold increase on day 7, and which then declined on days 14 and 28 (FIG. 9). To determine if TGF-β might be the factor in the conditioned media responsible for the induction of proteoglycan synthesis, the media was transiently acidified to activate TGF-β, and then added to normal cultured mesangial cells. The ability to stimulate proteoglycan production is a relatively specific property of TGF-β (Bassolis, A. and Massague, J., J. Biol. Chem. 263:3039–3045 (1988), which is incorporated herein by reference); thus, the response of the mesangial cell cultures to the conditioned media can be considered as a bioassay for TGF-β. Activated conditioned media from the nephritic glomeruli strongly stimulated proteoglycan production by normal mesangial cells (FIG. 10). The temporal pattern of proteoglycan synthesis induced by the conditioned media resembled the proteoglycan production seen in the glomerular cultures (compare FIGS. 9 and 10). Conditioned media that was not transiently acidified did not stimulate proteoglycan production.

Figure 11:
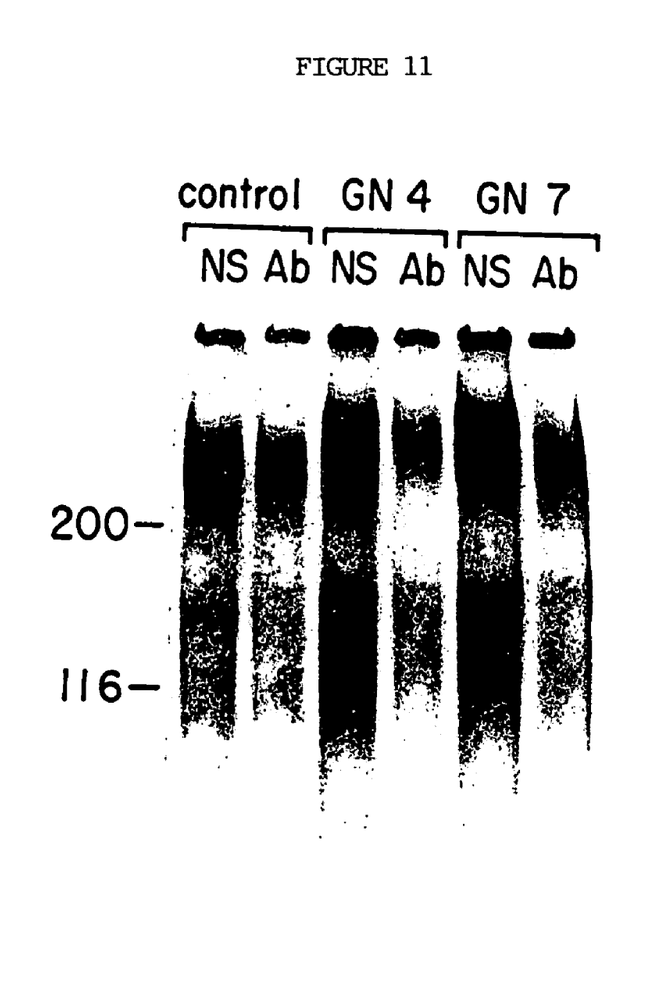
FIG. 11 shows the effect of anti-TGF-β synthetic peptide antibody on stimulation of proteoglycan production by conditioned media from nephritic glomeruli. Anti-TGF-β antibody (Ab) or normal preimmune serum (NS) was mixed with the conditioned media from nephritic glomeruli isolated on day 4 (GN 4) and 7 (GN 7) following injection of anti-thymocyte serum. The antibody reduced proteoglycan production by 77 percent (GN 4) and 68 percent (GN 7).
Figure 12:
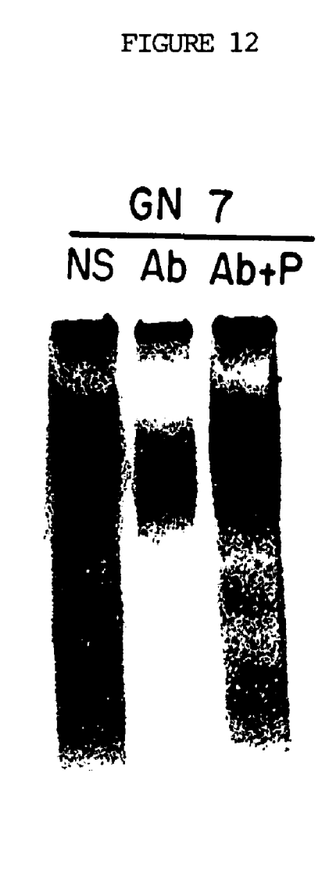

Further evidence of the presence of TGF-β was obtained by using antiserum raised against a synthetic peptide (TGF-β 78–109) from TGF-β. This antiserum was added to the conditioned media taken from glomerular cultures on days 4 and 7 following ATS injection. The TGF-β antiserum blocked the ability of the conditioned media to stimulate proteoglycan production (FIG. 11). Proteoglycan production by mesangial cells exposed to conditioned media from normal control glomeruli was also slightly reduced by the antiserum. Preincubation with the immunizing TGF-β synthetic peptide, abolished the blocking effect of the antiserum on the induction of proteoglycan synthesis by conditioned media from day 7 nephritic glomeruli (FIG. 12). In separate experiments, the TGF-β antiserum blocked the induction of proteoglycan synthesis, following addition of exogenous TGF-β to cultured mesangial cells; this effect was reversed after addition of the immunizing peptide, which also had no effect on proteoglycan induction when added to the condition media.

EXAMPLE V

Molecular Identification of Glomerular Proteoglycans

Figure 13:
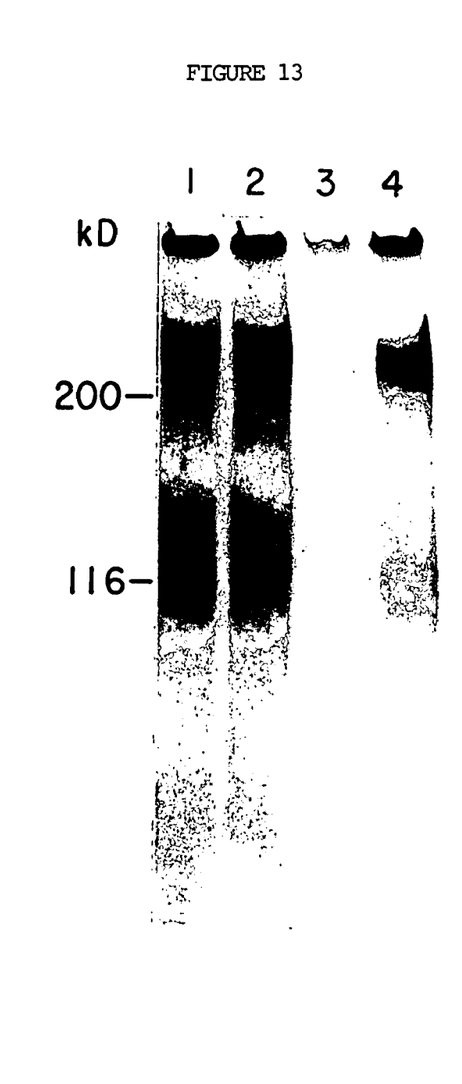
FIG. 13 shows enzymatic identification of the proteoglycans induced by conditioned media from nephritic glomeruli on day 7 following anti-thymocyte serum injection. Lane 1 is a control treated with saline. Lanes were treated with: heparinase II (lane 2), chondroitinase ABC (lane 3) and chondroitinase AC (lane 4). Complete digestion of the 220 kD and 120 kD bands is seen in lane 3 and partial digestion in lane 4, indicating the presence of chondroitin/dermatan sulfate proteoglycans.
Figure 14:
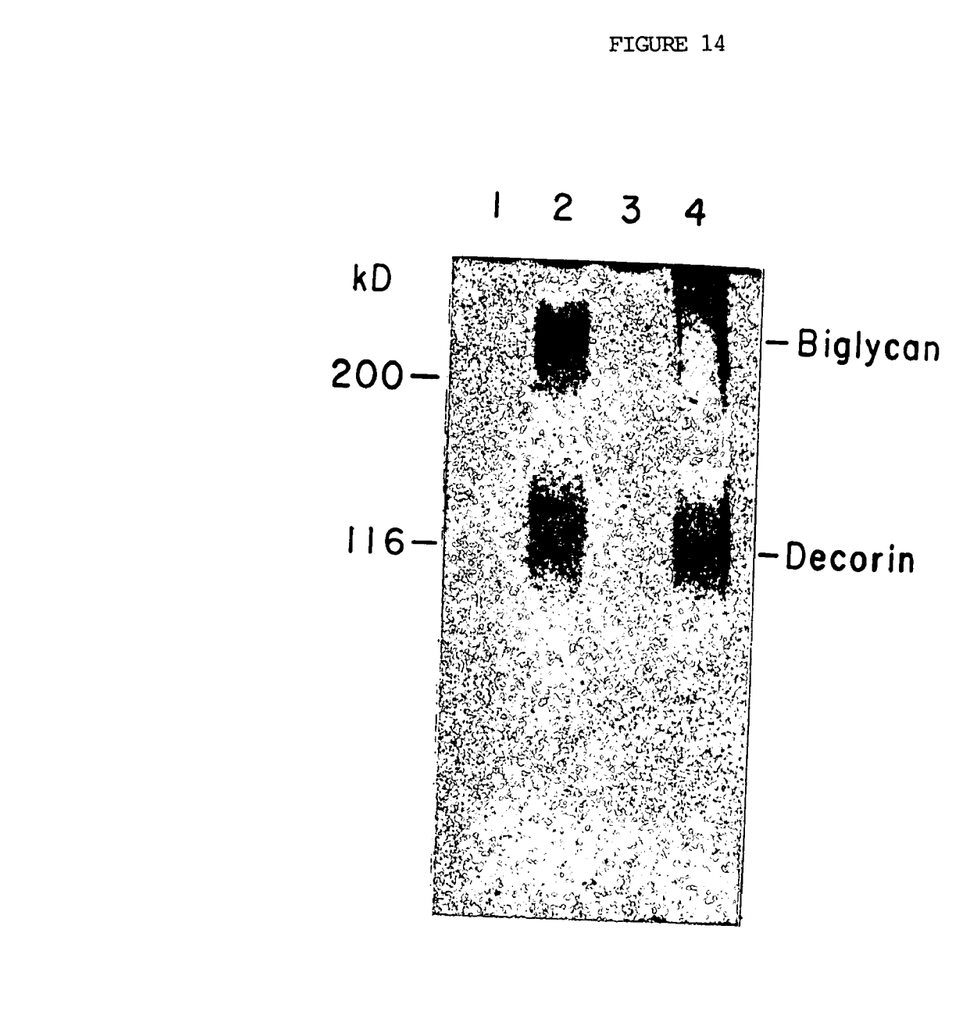

The proteoglycans present in the glomerular cultures were identified with antibodies and an enzyme digestion. Labeled condition media from the day 7 glomerular cultures was digested with specific enzymes or conditioned media after biosynthetic labeling as described in Example II. Samples for SDS-PAGE were mixed with sample buffer containing 3% SDS, 1 mM phenylmethylsulfonyl fluoride and 10% β mercaptoethanol and heated for 5 minutes at 100° C. as described above. Aliquots (20 μl) were equally applied to 4–12% gradient gels (Novex, Encinitas, Calif.). Molecular size markers were from Pharmacia (Uppsala, Sweden). Fluorography was performed by incubating gels in Enlightning (New England Nuclear). Typical exposure times for $^{35}S$ sulfate were 3 to 5 days. Fluorograms were scanned with an Ultrascan XL Enhanced Laser Densitometer (Pharmacia) to compare and quantitate the relative intensities and mobilities of the proteoglycan bands. The results showed that the induced small proteoglycans were fully sensitive to chondroitinase ABC and partially degraded by chondroitinase AC which indicates the presence of chondroitin/dermatan sulfate glycosaminoglycan chains (FIG. 13). Immunoprecipitation of the same medium with specific antibodies, identified the 220 kD band as biglycan and the 120 kD band as decorin (FIG. 14). The immunoprecipitation was performed as described in Example II and the samples analyzed by SDS-PAGE as described above.

The proteoglycans produced by the cultured mesangial cells in response to the conditioned media were identified as biglycan and decorin. These results are the same as observed following addition of exogenous TGF-β to normal rat mesangial cells in culture as described in Example II. The slight cross-reactivity of the anti-biglycan and decorin peptide antibodies seen in FIG. 14 is likely to be due to the closely related sequences of the two core proteins Fisher et al., J. Biol. Chem. 264:4571–4576 (1989), which is incorporated herein by reference).

EXAMPLE VI

Detection of Glomerular Cells Synthesizing TGF-β

Figure 15:
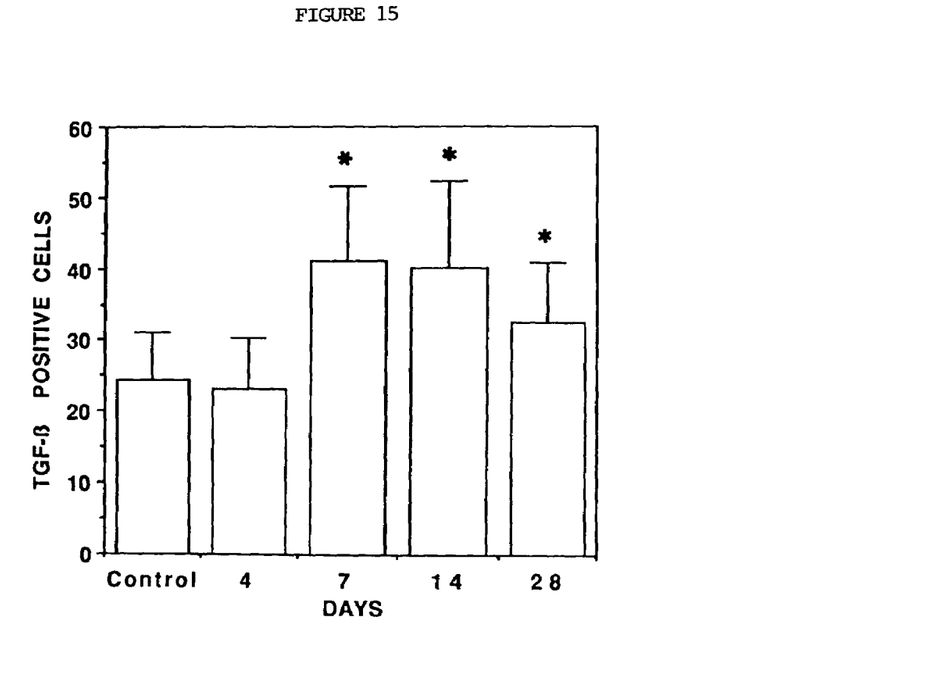
Figure 16A:
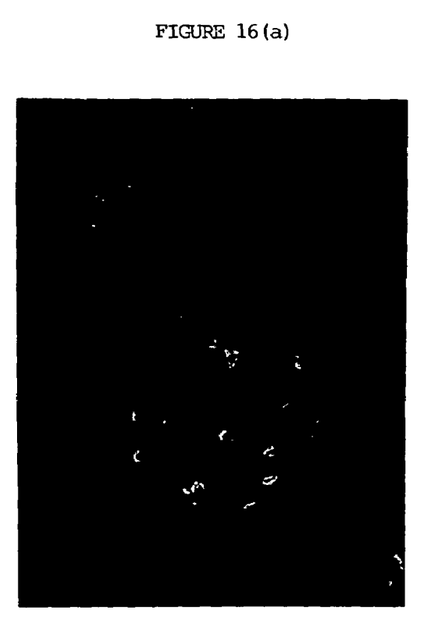
FIG. 16 shows immunofluorescence micrographs of glomeruli stained with anti-TGF-β antibody. There is a striking increase in the number of glomerular cells staining for TGF-β on day 7 (B) following induction of glomerulonephritis, compared to control (A) (×500).
Figure 16B:
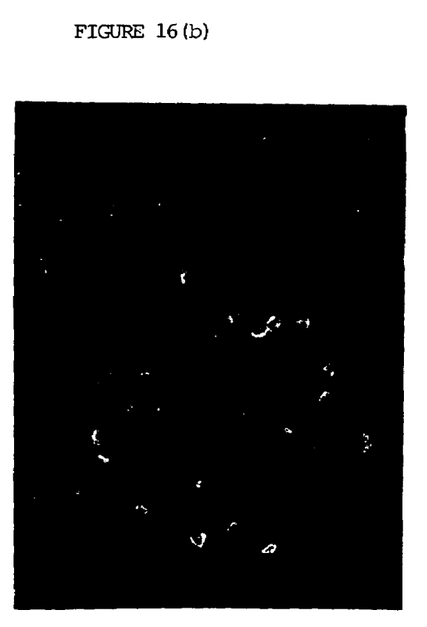

Anti-LC is an antibody made against a synthetic peptide from TGF-β that reacts with cells thought to be synthesizing TGF-β (Flanders et al. Biochemistry 27: 739 (1988). Anti-LC was used to detect TGF-β production by glomerular cells throughout the 28 day course of glomerulonephritis induced by ATS. Staining of glomeruli from normal control rats with this antibody showed an average of about 20 cells per glomerulus that were positive. In glomeruli from nephritic animals, the number of glomerular cells stained by anti-LC was unchanged on day 4 but doubled on day 7, the peak of glomerular proteoglycan production. The temporal pattern of the increase in the number of cells positive for TGF-β roughly parallels that of proteoglycan production by glomeruli and the conditioned media (FIG. 15). FIG. 16A shows a representative anti-LC staining pattern of a glomerulus from a normal control animal compared to that of an animal 7 days after ATS injection (FIG. 16B).

EXAMPLE VII

Figure 17A:
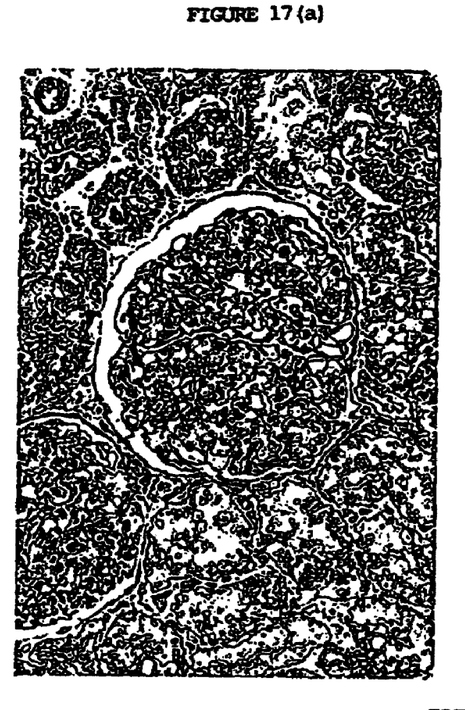
Figure 17B:
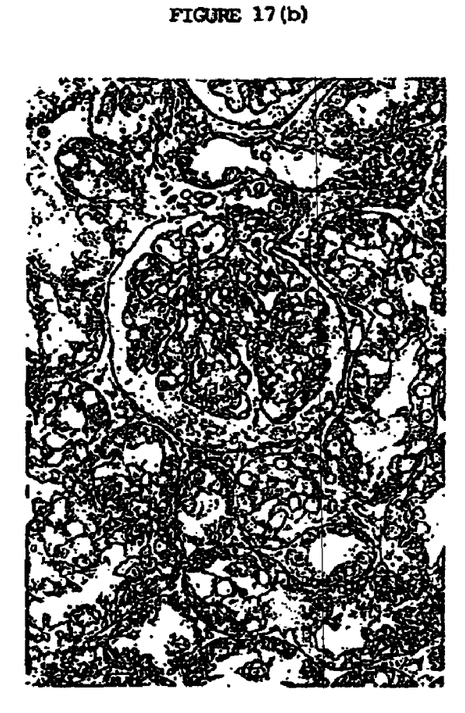
Figure 18:
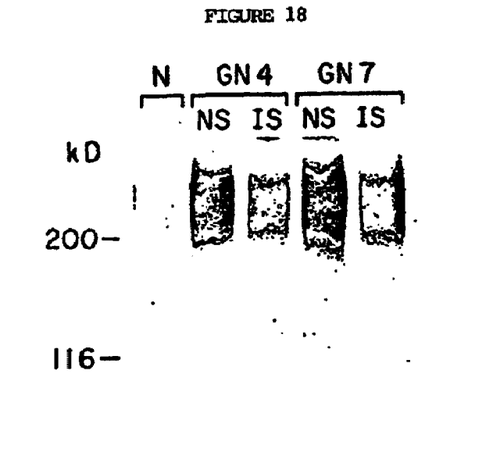
FIG. 18 shows proteoglycan synthesis by glomeruli from nephritic rats treated with TGF-β. Glomeruli were isolated 4 (GN4) and 7 (GN7) days after the injection of the anti-thymocyte serum that has been followed by treatments similar to those described in the legend of FIG. 17, and placed in culture. Proteoglycan synthesis was examined by labeling the cultures with $^{35}SO_4$ followed by analysis of the secreted products by SDS-PAGE and autoradiography. N3, nephritic rats treated with normal rabbit serum αTGF-β; IS nephritic rats treated with rabbit anti-TGF-β. The control lane (N) shows proteoglycan production in glomeruli from a normal kidney and the positions of molecular weight markers are indicated to the left.

Inhibition of Proteoglycan Synthesis in Nephritic Glomeruli with Anti-TGF-β Antibodies Nephritis was induced in rats with a single injection of ATS and the rats were then treated with either injections of anti-TGF-β (78–109) or normal rabbit serum as a control. Ten animals were used in each group in three different experiments. FIG. 17 shows a comparison of representative glomeruli from kidneys of treated and control animals. The glomeruli have expanded less and contain less extracellular matrix in the ant-TGF-β-treated group than in the normal rabbit serum controls. Biochemical analysis showed that proteoglycan production by glomerular cells, which is high in the cells from the injured kidneys was suppressed by anti-TGF-β (FIG. 18). Scanning of the gel bands in FIG. 18 and from other similar experiments indicated that the suppression of this measure of the disease process was about 50 to 65%. These results show that the disease was substantially attenuated by the anti-TGF-β treatment.

To gain information on the mechanism of the anti-TGF-βeffect, the level of TGF-β mRNA was examined in the kidneys of the treated and control rats. TGF-β can stimulate its own production (Van Obberghen-Schilling, et al., J. Biol. Chem. 263:7741 (1988), which is incorporated herein by reference). Therefore, an agent that inhibits the activity of TGF-β can also reduce its synthesis. The mRNA analysis revealed elevated levels of TGF-β mRNA in the nephritic rats including the anti-TGF-β treated animals. These results suggest that the antibody interrupted an paracrine loop of TGF-β activity.

EXAMPLE VIII

Inhibition of Proteoglycan Synthesis with an Arg-Gly-Asp Containing Peptide

Rat mesangial cells were grown to subconfluency in 6-well multiplates. The culture conditions and experimental protocol were as described in Example I. The cultures were made serum free for 24 hours and TGF-$β_1$ was added at 25 ng/ml along with Gly-Arg-Gly-Asp-Ser-Pro (GRGDSP) at 0.3, 0.1, 0.03, 0.01 or 0.003 mg/ml, or Gly-Arg-Gly-Glu-Ser-Pro (GRGESP) at 0.3 mg/ml. The peptides were synthesized as described in Pierschbacher and Ruoslahti, J. Bio. Chem., 292:1794–1798 (1987) which is incorporated by reference herein. Thirty hours later the cultures were metabolically labeled with $^{35}$S-sulfate and 18 hours afterward the conditioned media were analyzed by SDS-PAGE with fluorography. The fluorograms were scanned with a laser densitometer and the following represent relative densitometric units for the proteoglycan bands. Control 1.9, TGF-$β_1$ 4.5, TGF-$β_1$+GRGDS 0.3 mg/ml, 1.3, 0.1 mg/ml. 2.4, 0.03 mg/ml, 2.6, 0.01 mg/ml, 3.9, 0.003 mg/ml, 4.0 and GRGES 0.3 mg/ml, 4.3.

These data show a dose response effect of higher doses of GRGDSP causing inhibition of the TGF-$β_1$ induced proteoglycan production with no effect of the control peptide GRGESP.

Although the invention has been described with reference to the presently-preferred embodiment, it should be understood that various modifications can be made without departing from the spirit of the invention. Accordingly, the invention is limited only by the following claims.

We claim:

1. A method of decreasing the deleterious accumulation of extracellular matrix associated with a pathology or a condition wherein TGF-β-induced production and deleterious accumulation of extracellular matrix in a tissue exists comprising:

providing an anti-TGF-β antibody that binds to TGF-β; and contacting the tissue with the anti-TGF-β antibody that binds to TGF-β;

whereby the binding of the anti-TGF-β antibody to the TGF-β suppresses the deleterious accumulation of the TGF-β-induced extracellular matrix in the tissue, and wherein the pathology or condition is glomerulonephritis.

\* \* \* \* \*